(12) United States Patent
Bills et al.

(10) Patent No.: US 6,398,761 B1
(45) Date of Patent: Jun. 4, 2002

(54) DOUBLE SYRINGE BARRELS WITH PORTED DELIVERY ENDS

(75) Inventors: Dan J. Bills; Dan E. Fischer; Bruce S. McLean, all of Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 09/765,943

(22) Filed: Jan. 19, 2001

(51) Int. Cl.[7] ............................................... A61M 5/00
(52) U.S. Cl. ...................... 604/191; 604/82; 222/145.5; 433/90
(58) Field of Search .................. 604/191, 82, 83, 604/86, 88, 218, 416; 222/135, 137, 138, 145.5, 145.64; 466/88–90

(56) References Cited

U.S. PATENT DOCUMENTS

| | | |
|---|---|---|
| 4,767,026 A | 8/1988 | Keller et al. |
| 4,979,942 A | 12/1990 | Wolf et al. |
| 4,981,241 A | 1/1991 | Keller et al. |
| 5,038,963 A | 8/1991 | Pettengill et al. |
| 5,116,315 A | 5/1992 | Capozzi et al. |
| 5,137,182 A | 8/1992 | Keller et al. |
| 5,290,259 A | 3/1994 | Fischer |
| 5,301,842 A | 4/1994 | Ritter |
| 5,328,462 A | 7/1994 | Fischer |
| 5,370,273 A | 12/1994 | Rohloff et al. |
| 5,609,271 A | 3/1997 | Keller et al. ............. 222/145.6 |
| 5,643,206 A | 7/1997 | Fischer |
| 5,665,066 A | 9/1997 | Fischer |
| 5,697,903 A | 12/1997 | Fischer ....................... 604/82 |
| RE36,235 E | 6/1999 | Keller et al. |
| 5,918,772 A | 7/1999 | Keller et al. ............. 222/145.6 |
| 5,975,367 A | 11/1999 | Coelho et al. ............. 222/137 |

*Primary Examiner*—Anhtuan T. Nguyen
(74) *Attorney, Agent, or Firm*—Workman, Nydegger, Seeley

(57) ABSTRACT

The syringe system has a two separate pathways for delivering two materials for mixing. The syringe system has a plunger unit with two plungers that engage two barrels of a dual barrel cartridge to push the two materials into two separate lumens in a nipple on the dual barrel cartridge. The nipple has side portals for directing the materials away from each other as the materials are pushed out of the side portals. The nipple is inserted into a delivery chamber of a delivery tip that houses a static mixing element. The sidewalls of the delivery chamber mate with surfaces of the nipple such that the materials continue to have separate pathways after being pushed out of the side portals and reach the static mixing element.

23 Claims, 11 Drawing Sheets

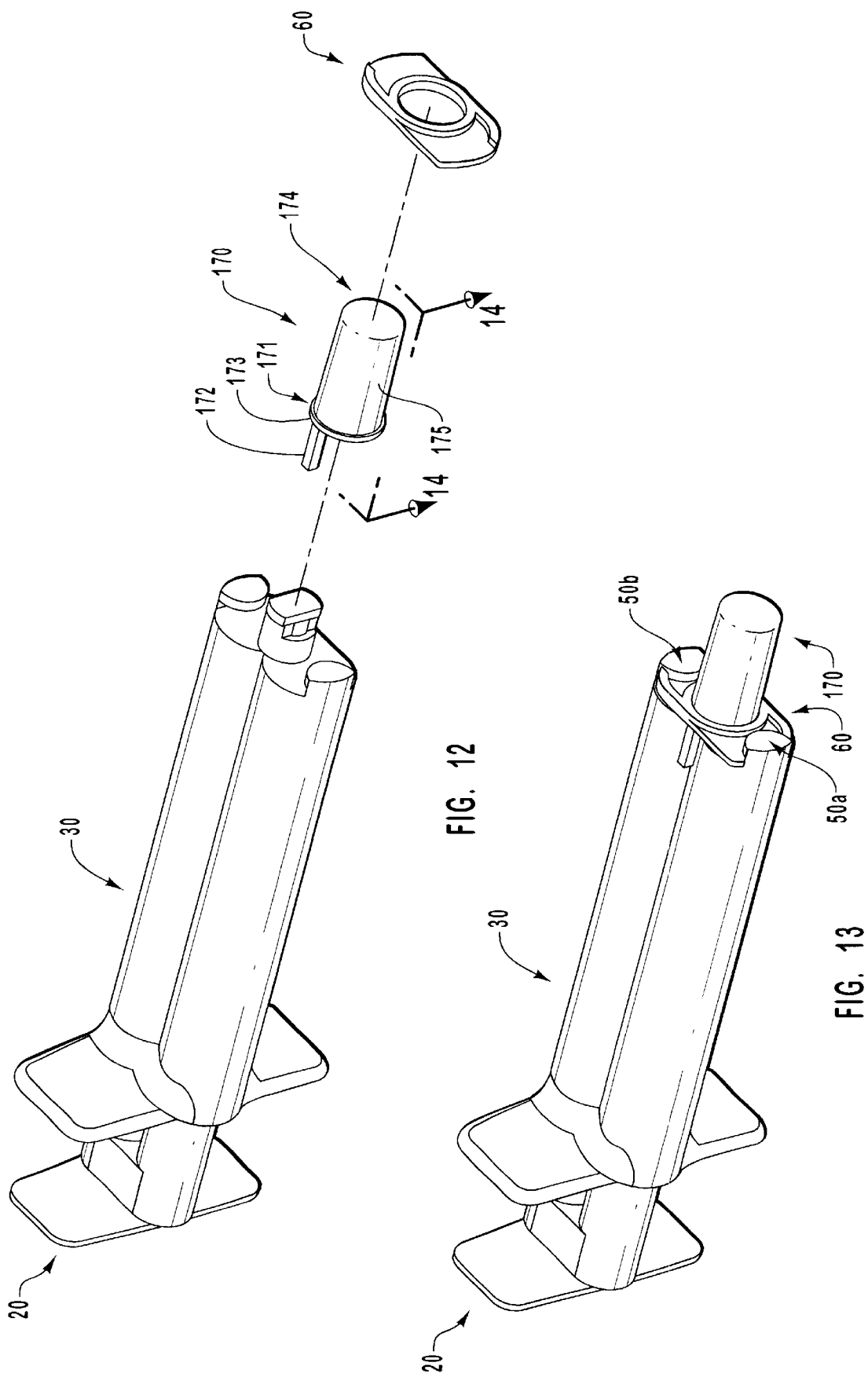

DOUBLE SYRINGE BARRELS WITH PORTED DELIVERY ENDS

BACKGROUND OF THE INVENTION

1. The Field of the Invention

This application is directed to methods and devices for delivering multi-part compositions. More particularly, the application is directed to syringes and delivery tips for delivering multi-part medical and dental compositions.

2. Relevant Technology

Many modern formulations are packaged in two parts, often known as "A/B components" or "first and second materials". Upon mixing, these A/B components typically undergo a chemical reaction which causes the resultant composition to "set up" in some desired manner, for example, by forming a hardened material. In the dental field, for example, several two-part formulations currently enjoy wide use, such as glass ionomer cements and resinous luting cements. Dental impression materials are also typically made using A/B components.

In order to function properly, it is important that the A/B components of these two component systems be separated until it is desired to mix the components. Typical techniques for retaining A/B type materials in a separated state before mixing the materials include loading the A/B materials into two-part material delivery apparatuses having separate side-by-side barrels or tubes. The side-by-side barrels are each configured to receive a separate material therein and deliver the separate material therefrom Examples of such two-part material delivery apparatuses having side-by-side barrels are disclosed in U.S. Pat. Nos. 5,290,259; 5,328,462; 5,643,206; 5,665,066; and 5,697,903, assigned to Ultradent Products, Inc., each of which is incorporated by reference herein. A wide variety of such two-part material delivery apparatuses exist. Such apparatuses typically have a proximal material receiving end, and a distal delivery end. The distal delivery end typically features first and second openings which are adjacent one another and which are located at the end of neighboring barrels. Material delivered from one of the adjacent openings is typically delivered next to and in parallel relationship with the material delivered from the other opening.

Upon delivery of the first and second materials through the adjacent openings, the practitioner can then mix the materials in a mixing bowl, syringe, mixer or other device. Although mixing of the A/B materials is the ultimate goal of A/B type delivery systems, premature mixing and hardening of material is generally detrimental. Nevertheless, in typical A/B type delivery systems, it is common for a certain amount of undesired commingling of A/B type materials to occur as the A/B materials exit the adjacent first and second openings. Sometimes, some of the mixed material contacts the distal delivery end of the delivery system, such as by depositing on one of the edges of the proximal and distal openings. Such mixed material tends to harden on the delivery system.

If mixed material hardens in an opening, the hardened material can block or impede the flow path of a barrel. The disruption of the normal flow pattern can cause additional mixing and hardening in undesired areas. Thus, the buildup of reactive A/B materials on the distal end of a delivery system can slow, stop, or otherwise disrupt the delivery of the materials through the system.

The problem of material build up becomes particularly acute when a delivery system is used, then temporarily set aside or stored before a subsequent use. This allows time for mixed materials to harden before the subsequent use.

Another problem associated with the delivery of A/B materials is that uncovered delivery ends can dry out or become inadvertently contaminated. While it is possible to cover delivery ends with a cap, such caps can become readily separated from the delivery system and lost. Furthermore, it can be difficult to achieve a reliable seal between a delivery tip and a two-part material delivery apparatus which delivers material to the delivery tip, thereby allowing seepage of material at the junction between the tip and the two-part material delivery apparatus.

There is, therefore, a need in the art for a system for delivering A and B type materials which keeps the materials separate until mixing is desired and thereby avoids cross-contamination and hardening of the materials until the desired time. Specifically, there is a need in the art for a system which avoids cross-contamination between two materials at a distal delivery end of the system.

There is also a need in the art for an improved seals within the material delivery systems to prevent co-mingling of the A/B materials as the materials are delivered for mixing or during storage. Furthermore, there is a need in the art for an improved system for covering the delivery end of the system during storage.

SUMMARY AND OBJECTS OF THE INVENTION

It is therefore an object of the invention to provide an improved delivery system for delivery of A/B type materials.

It is another object of the invention to provide an improved system for delivering A and B type materials which keeps the materials separate until mixing is desired and thereby avoids cross-contamination and hardening of the materials until the desired time. Specifically, it is an object of the invention to provide a system which avoids cross-contamination between two materials at a distal delivery end of the system It is another object of the invention to provide an improved seals within the material delivery systems to prevent co-mingling of the A/B materials as the materials are delivered for mixing or during storage.

It is another object of the invention to provide an improved cap for covering the delivery end of the system when not in use.

These objects are achieved through an inventive syringe system for mixing first and second materials together and delivering the mixed materials. The syringe system has a dual barrel cartridge with a uniquely configured dual lumen nipple that is removably coupled with a uniquely configured tip. When the tip is positioned on the dual lumen nipple of the dual barrel cartridge, two separate flow paths are created so that the A/B materials remain separated until being brought together for mixing in the tip.

The dual barrel cartridge has a proximal grasping end opposite from a distal delivery end. The dual barrel cartridge has two barrels that each having an opening at the proximal grasping end of the dual barrel cartridge and a barrel outlet at the distal delivery end of the dual barrel caridge. A plunger unit with two plungers is inserted into the two barrels of the dual barrel cartridge.

The dual barrel cartridge has opposing claws at its distal delivery end which engage a removable collar. The removable collar holds the tip on the nipple once the tip has been inserted though an aperture of the removable collar and the collar locked under the claws of the dual barrel cartridge.

The dual lumen nipple has a receiving end opposite from a terminal end. The dual lumen nipple has cylindrical sidewalls that extend integrally from the distal delivery end of the dual barrel cartridge. The lumens are preferably divided by a septum that extends integrally from the distal delivery end of the dual barrel cartridge and across the sidewalls. Each lumen is in fluid communication with one of the barrels of dual barrel cartridge through the barrel outlets. The sidewalls of the nipple are partially terminated such that each lumen has a side portal.

As the plungers are depressed into the barrels, the first and second materials are respectively pushed through the barrel outlets and into lumens of the dual lumen nipple. The materials are then pushed out of the lumens via the side portals of the lumens. Each side portal has a top defined by a flat sealing head that extends at the terminal end of the dual lumen nipple from the septum and a portion of the sidewalls. The flat sealing head preferably has truncated flanges that extend perpendicularly relative to the septum Each truncated flange has a length that permits the material delivered out of each side portal to pass around the truncated flange when the nipple is inserted into the delivery chamber of the tip.

The delivery tip has a proximal coupling end opposite from a distal delivery end. The delivery tip has a hub at its proximal coupling end that is integrally connected to a mixing element housing. The mixing element housing has a mixer chamber in which a static mixing element is housed. The tip is preferably designed to enable the materials to separately enter the static mixing element.

The hub of the delivery tip has hub sidewalls and a hub shoulder extending inward from the hub sidewalls to the mixing element housing. The hub also has a delivery chamber that is sized to receive the nipple in a releasable manner. The delivery chamber has a delivery chamber opening that is opposite from a mixing chamber inlet. The mixing chamber inlet is the opening into the mixing chamber and enables the delivery chamber to be in fluid communication with the mixing chamber.

The hub sidewalls have interior surfaces that include opposing raised sidewall portions between opposing sidewall channels. Similarly, the hub shoulder has interior surfaces that include opposing raised shoulder portions between opposing shoulder funnels. The opposing raised sidewall portions and the opposing raised shoulder portions are aligned and adapted to form a seal with the sidewalls and the flat sealing head of the nipple once the nipple is inserted into the delivery chamber. The opposing sidewall channels are aligned with the opposing shoulder funnels such that there is a separate pathway for each material from each side portal to the mixing chamber inlet.

Upon reaching the mixing chamber inlet, the materials are preferably still separate from each other. The mixing element is preferably positioned with its first vane in the mixing chamber inlet. The first vane has a leading edge that is positioned such that the leading edge extends between the opposing raised shoulder portions of the hub shoulder, is centered on the opposing raised shoulder portions and is flush with the opposing raised shoulder portions while extending slightly beyond the opposing shoulder funnels. This configuration enables the leading edge to be tightly pressed up against the flat sealing head. The leading edge of the first vane may even be pressed firmly enough to form a seal with the flat sealing head. After the materials pass through the first vane without contact each other, then they enter the second vane which is oriented such that the materials contact each other and the mixing process begins. After passing through the series of vanes of the mixing element, then the two materials are fully mixed together and exit as a mixed material from the mixing element housing.

The system also includes a cap for insertion over the nipple after the delivery tip has been removed. Like the tip, the cap has surfaces that engage the side portals and surfaces that form a seal with the sidewalls and the flat sealing head of the nipple once the nipple is inserted into the nipple chamber of the cap. This enables the materials held in the barrels to be sealed for later use.

As indicated above, one of the advantages achieved through these features is that materials separately exit the dual lumen nipple of the double barrel cartridge and continue to be maintained in separate pathways even after being delivered into the nipple. More particularly, the pathways remain distinct until after the materials enter the mixing element. This eliminates the potential for cross-contamination and hardening of the materials before use of the materials is desired.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which:

FIG. 12 is an exploded perspective view of a two-part material delivery syringe system with a cap.

FIG. 13 is a perspective view of the two-part material delivery syringe system as shown in FIG. 12.

DETAILED DESCRIPTION OF THE PREFERRED EMBODIMENTS

Figure 1:
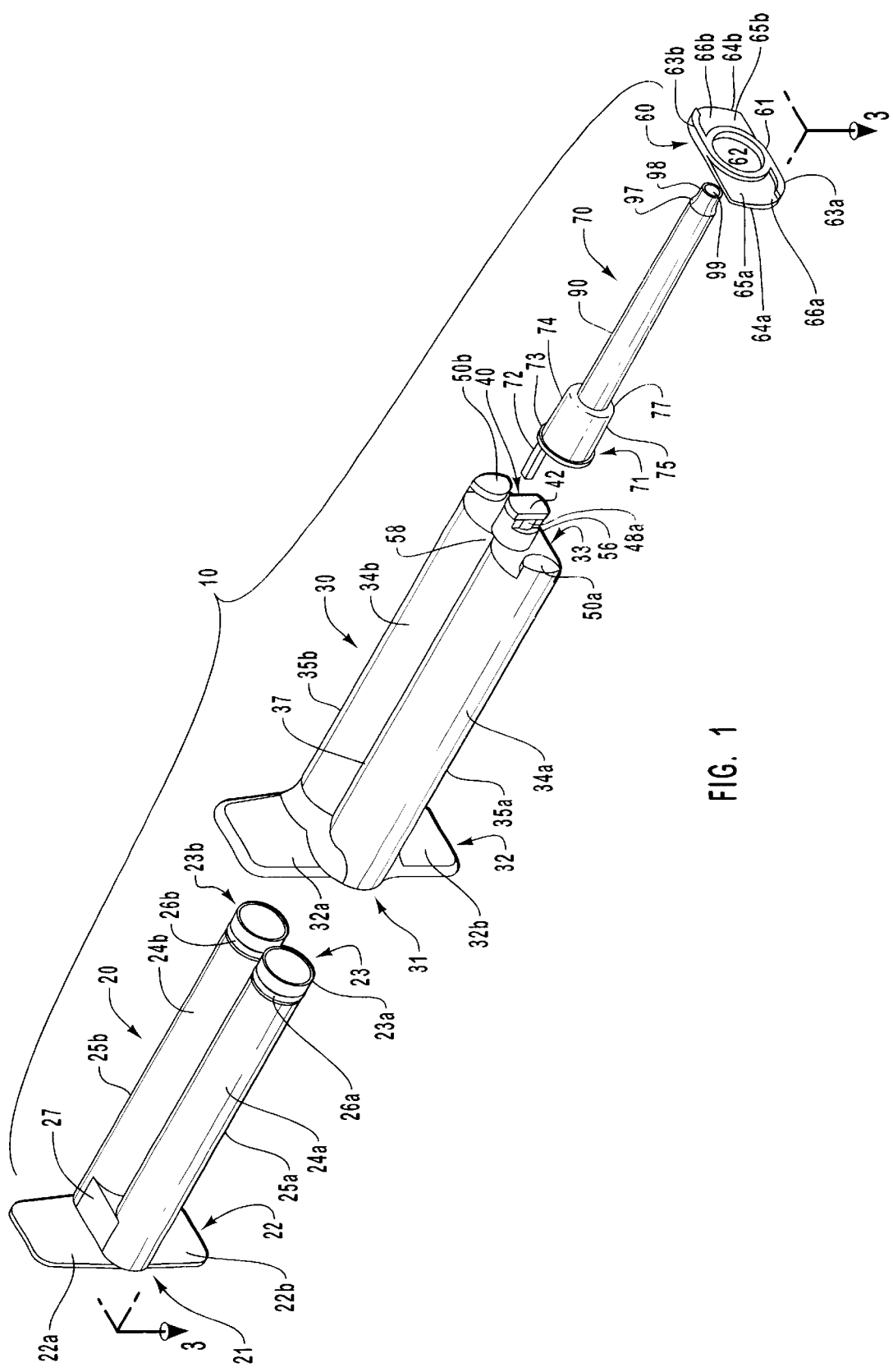
FIG. 1 is an exploded perspective view of a two-part material delivery syringe system.

FIGS. 1–15 depict an example of a two-part material delivery syringe system at 10. The main components of syringe system 10 include a dual plunger unit 20, a dual barrel cartridge 30, a retention collar 60 and a tip 70. The main elements of dual barrel cartridge 30 include barrels 34a–b, dual lumen nipple 40 and collar retainers or tabs 50a–b. Collar retainers 50a–b cooperate with collar 60 to hold tip 70 in place. Note that tip 70 can be replaced by a cap 170 as shown in FIGS. 12–15. The two-part material delivery syringe is intended for use with any two-part composition such as those discussed above. All of these components and their elements are described below in detail after a description of their general interrelationship.

Figure 2:
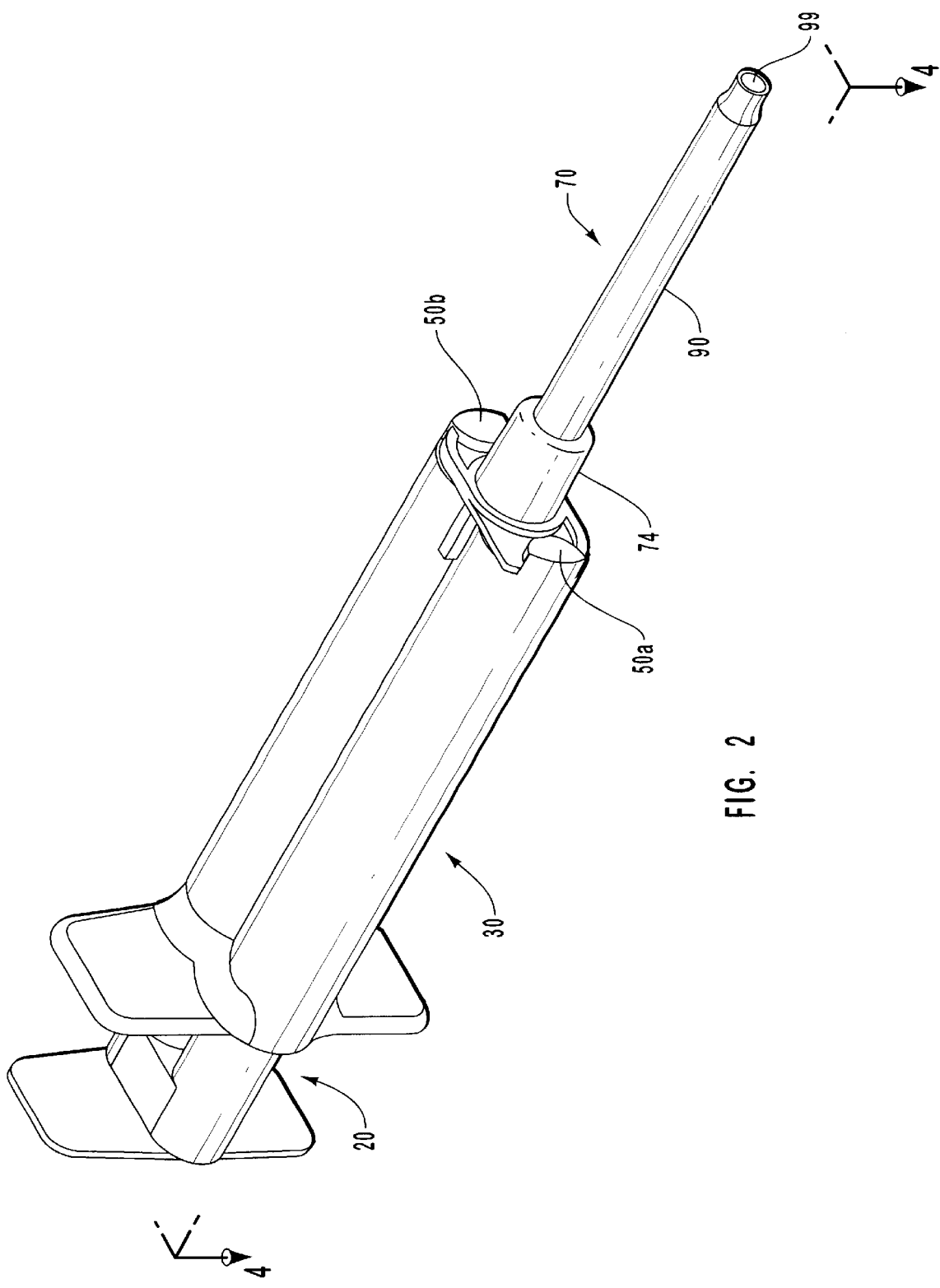
FIG. 2 is a perspective view of the two-part material delivery syringe system as shown in FIG. 1.
Figure 3:
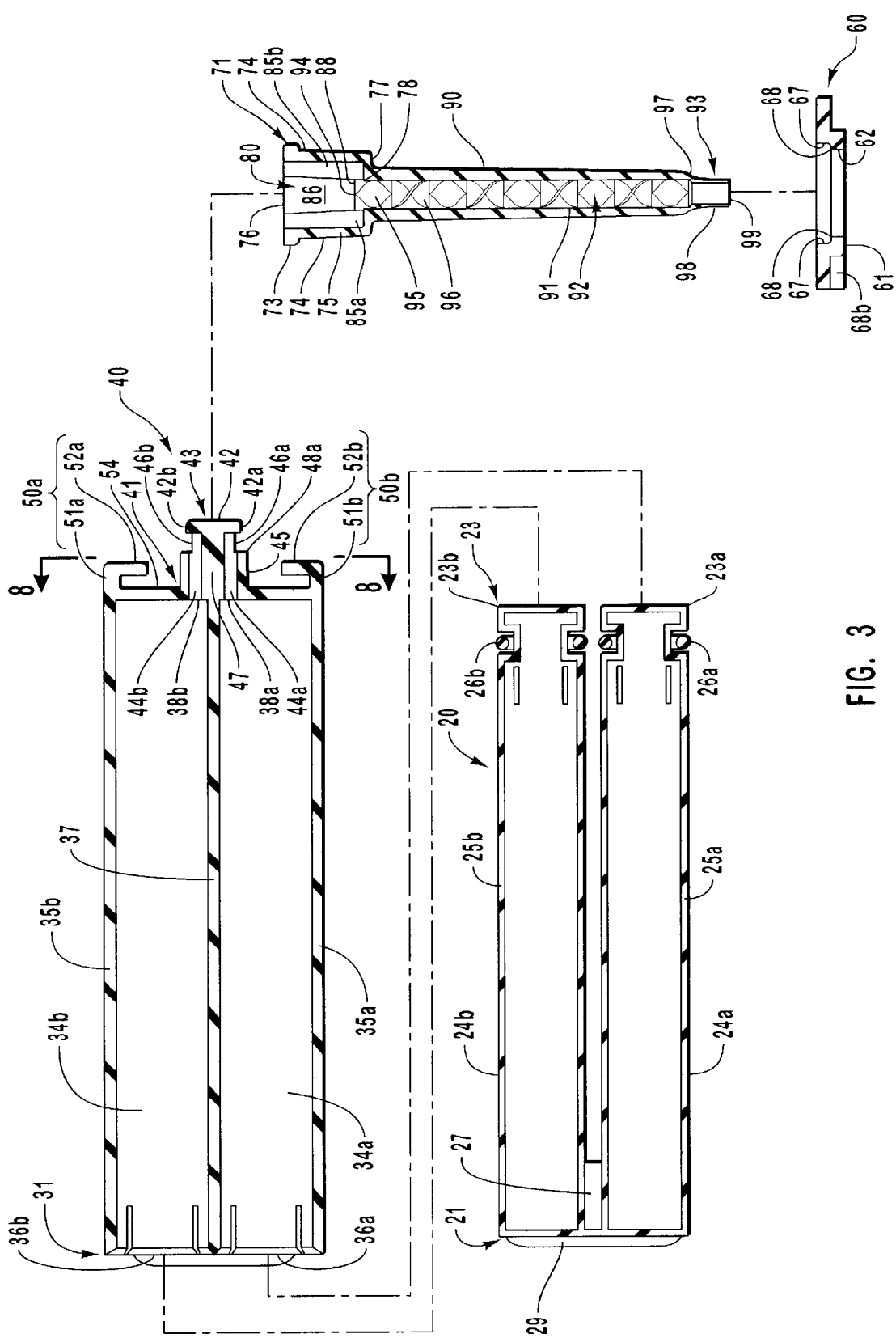
FIG. 3 is an exploded, longitudinal, cross-sectional view of the two-part material delivery syringe system as shown in FIG. 1 taken along cutting lines 3—3 in FIG. 1.
Figure 4:
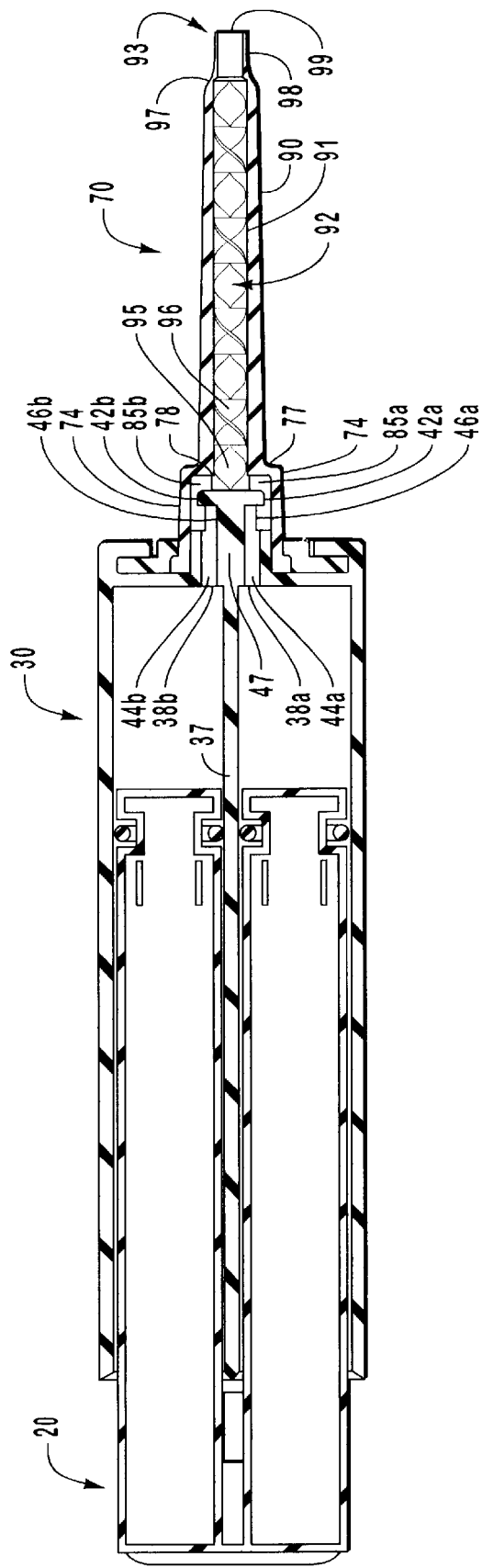
FIG. 4 is a longitudinal, cross-sectional view of the two-part material delivery syringe system taken along cutting lines 4—4 in FIG. 2.
Figure 6:
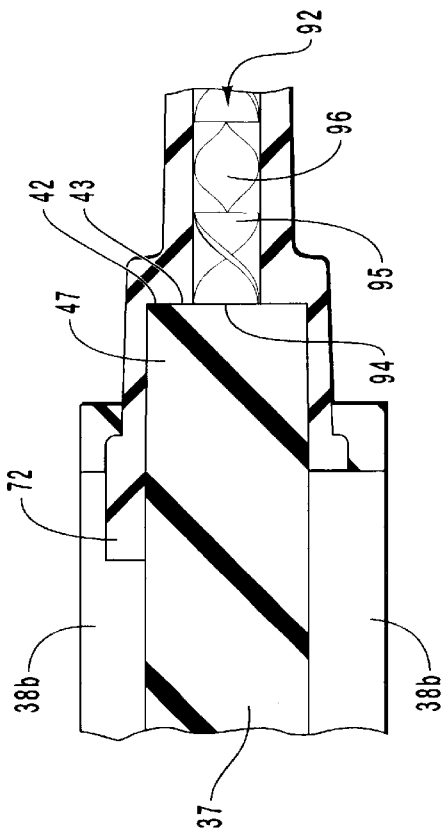
FIG. 6 is an enlarged, cross-sectional, partial view of the two-part material delivery syringe system taken along cutting lines 6—6 as shown in FIG. 5 to depict the same elements shown in FIG. 5 from a different plane.
Figure 5:
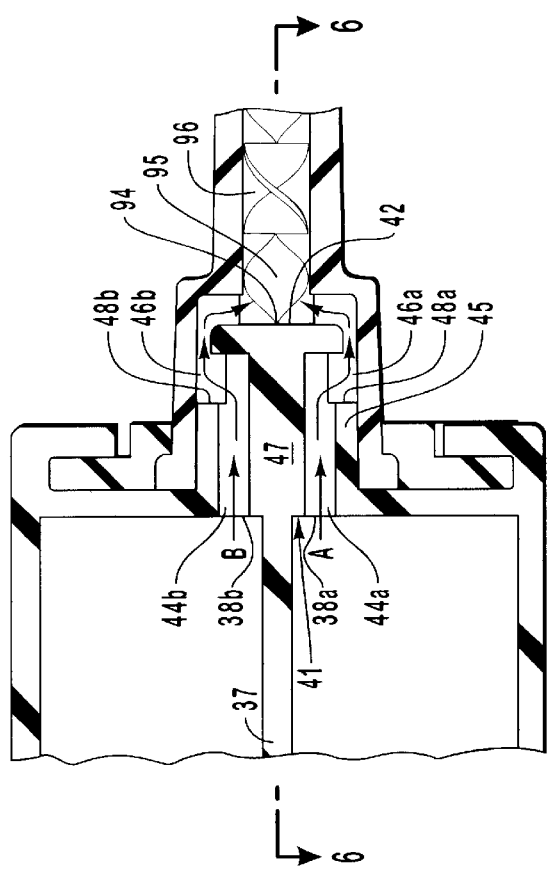
FIG. 5 is an enlarged, partial view of the cross-sectional view shown in FIG. 4 of the two-part material delivery syringe system.
Figure 7:
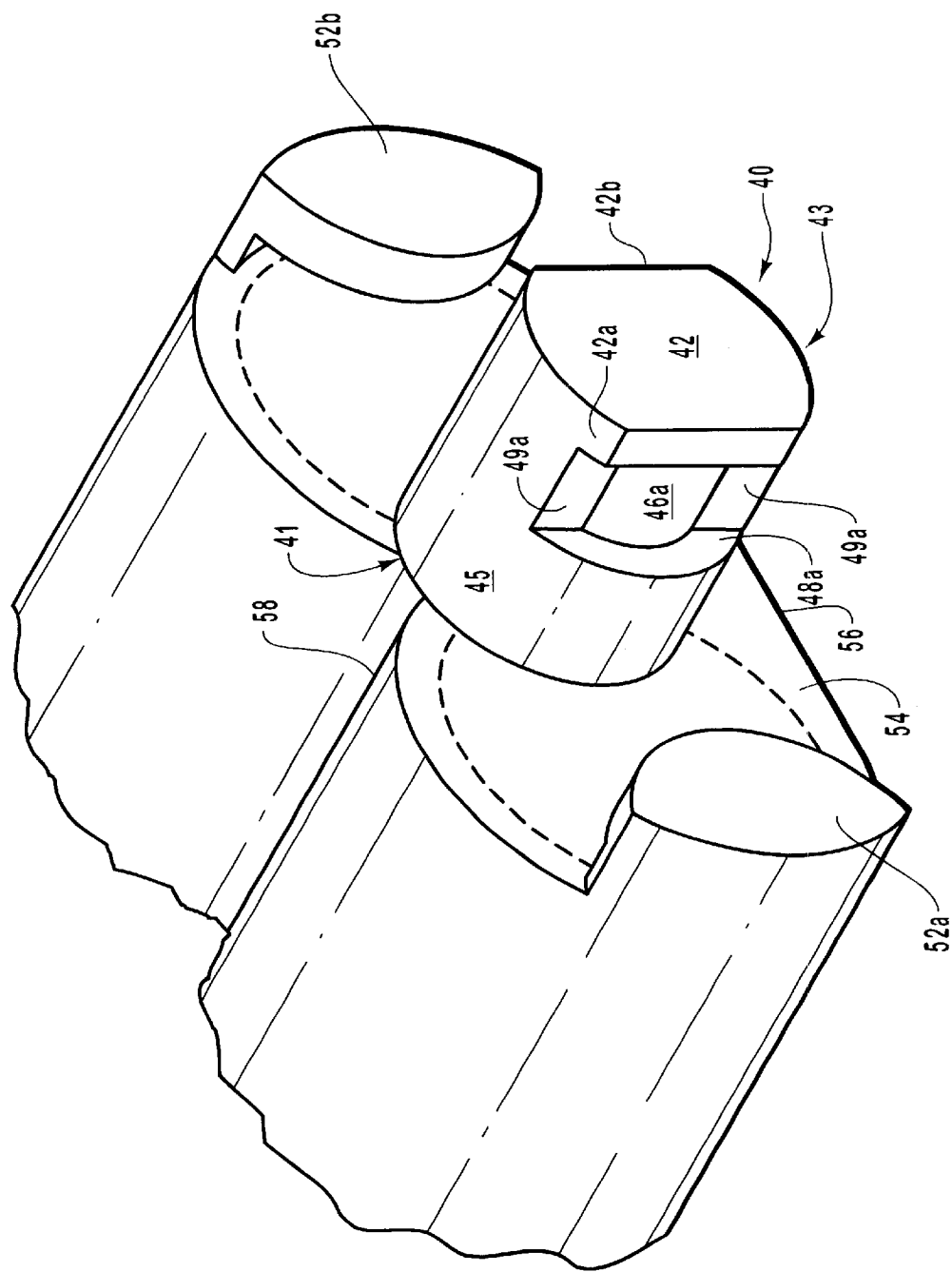
FIG. 7 is an enlarged view of the nipple at the distal delivery end of the dual barrel cartridge.

Two-part material delivery syringe system 10 is shown in FIG. 1 in an exploded view and then assembled in a perspective view in FIG. 2. The same system is shown in FIG. 34 in cross sectional views that respectively show syringe system 10 in exploded and assembled views. FIG. 5 is an enlarged view of nipple 40 and hub 74 of distal delivery tip as shown in FIG. 4 that shows the flow paths between nipple 40 and hub 74. FIG. 6 depicts the same elements as shown in FIG. 5 cut from a different plane to show the seals between nipple 40 and hub 74. With references to FIGS. 1–6, dual plunger unit 20 has two plungers 24a–b adapted for insertion into the corresponding barrels 34a–b of dual barrel cartridge 30. Depressing plungers 24a–b into barrels 34a–b drives a first material, material A, and a second material, material B, held respectively in barrels 34a–b into dual lumen nipple 40. More particularly, as pressure is applied to materials A and B, the materials are respectively pushed through barrel outlets 38a–b, into nipple lumens 44a–b and then out of side portals 46a–b and into tip 70. In one embodiment, plungers 24a–b are depressed while slowly, simultaneously withdrawing tip 70 from within a container, such as a syringe barrel, for subsequent delivery. In another embodiment, syringe system 10 is used to directly deliver the mixtures of materials A and B onto a substrate.

Plunger unit 20 comprises a first plunger 24a and a second plunger 24b. Plunger unit 20 has a proximal pushing end 21 with a pushing handle 22 opposite from a distal lead end 23. Distal lead end 23 is more accurately referred to as distal lead ends 23a–b of plungers 24a–b. Plungers 24a–b have respective sidewalls 25a–b that are sized to engage sidewalls 35a–b of barrels 30a–b in a manner such that a seal is created. The ability to form an effective seal is enhanced by the use of a o-rings such as o-rings 26a–b shown at distal lead ends 23a–b. Note, however, the distal lead ends 23a–b may have many varying configurations depending on the types of materials being delivered. Proximal pushing end 21 may also have any suitable configuration. However, a stabilizing bridge 27 is preferably located at proximal pushing end 21 between first plunger 24a and second plunger 24b for maintaining their alignment. The plungers 24a–b may also alternatively be held together without a stabilizing bridge by pushing handle 22. However, pushing handle 22 is preferably configured, as shown, with two annular flanges 22a–b extending perpendicularly outward from stabilizing bridge 27. An insert 29 is positioned within a cavity at proximal pushing end 21. Insert 29 may be color coded to indicate the identity of the materials held in barrels 34a–b.

Dual barrel cartridge 30 has a proximal grasping end 31 with a grasping handle 32. Opposite from proximal grasping end is distal delivery end 33 from which nipple 40 extends. is Dual barrel cartridge 30 comprises first and second barrels 34a–b that have tubular sidewalls 35a–b. Barrels 34a–b preferably share a common septum as shown at 37 which is formed by their sidewalls 35a–b. Use of such a septum reduces the amount of material needed to form dual barrel cartridge 30, however the barrels can also be separate without a common septum Each barrel 34a–b has an opening 36a–b at proximal grasping end 31 and a barrel outlet 38a–b at distal delivery end 33. Barrels 34a–b and the other downstream components are shown having the same size for mixing materials in a ratio of 1:1, however, it is also possible to utilize the present invention for mixing materials in other ratios.

Grasping handle 32 comprises two annular flanges 32a–b extending perpendicularly outward from sidewalls 35a–b at proximal grasping end 31 of dual barrel cartridge 30. The grasping handle may alternatively have a round configuration. Grasping handle 32 may be configured as shown so that openings 36a–b are partially defined by the two annular flanges 32a–b of grasping handle 32 or such that the handles extends all the way around openings 36a–b. Dual barrel cartridge 30 is an example of barrel means for holding the first and second materials in separate barrels until pressure is applied with sufficient force to direct the first and second materials out of barrel outlets.

It should be understood that the primary function of dual lumen nipple 40 is deliver materials A and B into tip 70. However, this delivery is preferably achieved with minimal cross-contamination of one material with the other. Dual lumen nipple 40 has several features that assist in minimizing the potential for cross-contamination. Herein below is a description of the structure of nipple 40 followed by an explanation of the advantages provided by these structures.

Dual lumen nipple 40 extends integrally at its receiving end 41 from distal delivery end 33 of dual barrel cartridge 30. Dual lumen nipple 40 has a flat sealing head 42 located at its terminal end 43, which is opposite from terminal end 43. Dual lumen nipple 40 is best understood with reference to FIGS. 1–6 for general orientation and with reference to FIGS. 7–8 for specific details.

Nipple 40 has two nipple lumens 44a–b that are in fluid communication respectively with barrels 34a–b. The openings into lumens 44a–b are barrel outlets 38a–b. Lumens 44a–b are preferably divided from each other by a septum 47, however it is also possible for the lumens to be separate from each other without a common septum. Materials A and B exit lumens 44a–b through side portals 46a–b as the materials encounter the truncated flanges 42a–b that extend integrally from the flat sealing head 42 and perpendicularly relative to septum 47. As indicated above, materials A and B are respectively pushed out of side portals 46a–b for delivery into tip 70 and then for mixing in tip 70.

Figure 8:
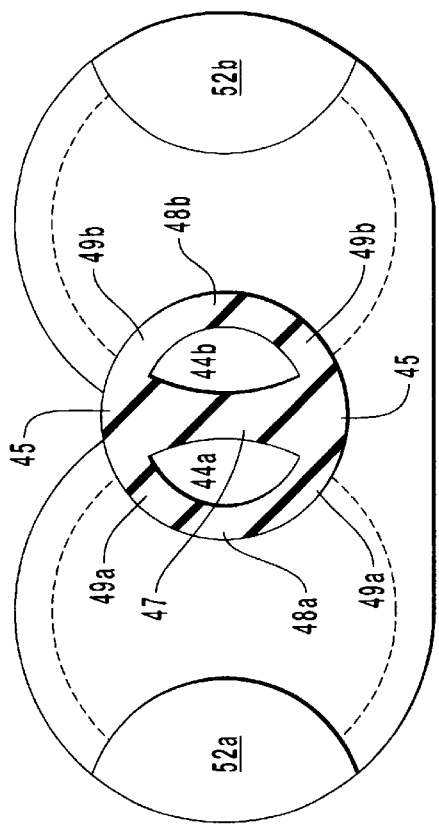
FIG. 8 is a transverse cross-sectional view of the nipple shown in FIG. 1 taken along cutting lines 8—8 in FIG. 3 to depict the configuration of nipple 40 when cut at the bottom or the windowsill of each of the side portals.

Nipple 40 has sidewalls 45 that extend integrally from distal delivery end 33. As discussed below, portions of sidewalls 45 extend from receiving end 41 of nipple to its terminal end 43. Sidewalls 45 define the interior surfaces 45a–b on the exterior sides of lumens 44a–b that are opposite from septum 75. As shown, first and second lumens 44a–b of dual lumen nipple 40 each have a generally semicircular cross-sectional. However, the lumens may have any suitable shape. The septum 47 shared by lumens 44a–b may also have any suitable configuration. The sides of septum 47 may be concave as shown in FIG. 8, which is cross-sectional view of nipple 40 taken through side portals 46a–b, for ease in manufacturing. The sides of septum 47 may also have other suitable configurations. For example, the sides of septum 47 may be flat. As shown, septum 47 extends integrally from sidewalls 45.

Slightly more than half way up from receiving end 41, sidewalls 45 partially terminate to define the bottoms of side portals 46a–b. The bottom or windowsill of each of the side portals 46a–b are identified at 48a–b. The sides of side portals 46a–b are preferably defined by small extension of sidewalls 45 that extend from the portions of sidewalls 45 from which septum 47 extends, these referred to herein as seal extensions 49a–b. The tops of side portals 46a–b are defined by truncated flanges 42a–b.

Sidewalls 45 of dual lumen nipple 40 have a tapered cylindrical configuration to engage tip 70 in manner such that there is a fluid-tight seal formed between sidewalls 45 and the corresponding tapered surfaces of tip 70. In a preferred embodiment, the slight taper is. an approximately 1.7° taper. Note that seal extensions 49a–b, which are also extensions of sidewalls 45, have a cylindrical configuration with the same taper as the remainder of the sidewalls below seal extensions 49a–b. So nipple 40 tapers in diameter from receiving end 41 to terminal end 43. While the entire nipple 40 may be described as having a tapered cylindrical configuration, it should be recognized that flat sealing head 42 is only partially cylindrical. It has opposing round ends, however, the ends of truncated flanges 42a–b extend from septum 47 to their respective terminal ends with a length that is less than the largest radius between the exterior or outer diameter of the sidewalls 45. Accordingly, the shape of flat sealing head 42 may also be described as a circle truncated at opposing cords of equal length. The configuration of truncated flanges 42a–b enables materials A and B to pass around truncated flanges 42a–b and into tip 70.

As indicated above, side portals 46a–b are defined by sidewalls 45 at its bottom 48, by seal extensions 49a–b on its sides and by truncated flanges 42a–b at its top. There are several advantages achieved by this configuration that relate to maintaining the separation of materials A and B until the materials are in tip 70. To minimize the potential for cross-contamination the distance between side portals 46a–b is preferably maximized for either material to pass out of one side portal and go around the nipple to the other side portal. More particularly, the distance is preferably maximized between a side of a side portal and a side of the other side portal. The maximized distance between the side portals 46a–b is balanced against the ability to express materials A and B out of lumens 44a–b. This balance is optimized by limiting the width of side portals 46a–b such that their sides are defined by seal extensions 49a–b and not by just the portions of the sidewalls from which septum 47 extends. Seal extensions 49a–b increase the width of the barrier provided by just the portions of the sidewalls from which septum 47 extends. Of course, it is possible for another embodiment to have wider side portals without seal extensions, however, this increases the risk of cross-contamination. Nipples having side portals that are so wide that there are no seal extensions still form a seal when inserted into a delivery chamber of a delivery tip as there are opposing portions of the sidewalls on the opposite ends of the septum that extend to terminal end 43.

As mentioned above, truncated flanges 42a–b extending perpendicularly from septum 47. The perpendicular orientation of truncated flanges 42a–b assists in directing materials A and B away from each other as they exit the respective side portals 46a–b. Truncated flanges 42a–b may have many suitable configurations that assist in directing the materials away from each other in nonparallel directions. For example, septum 47 may flare outwardly with respect to the longitudinal axis of septum 47 such that it gradually widens as delivery end 31 is approached. Of course, truncated flanges 42a–b may also be eliminated in another embodiment such that the sealing head is merely the top of the septum. However, truncated flanges 42a–b are preferably utilized since their presence assists in preventing materials A and B from passing over septum 47 to prematurely contact each other. Whether nipple 40 has a flat sealing head 42 with truncated flanges or not, sidewalls 45 extend from receiving end 41 to flat sealing head 42 at terminal end 43 such that the entire base of nipple 40 is cylindrical as well as the portion of sidewalls 45 in between side portals 46a–b.

Nipple 40 is selectively coupled in fluid communication with proximal coupling end 71 of tip 70 via a collar 60 and cooperating components of dual barrel cartridge 30, as shown in FIGS. 1–6. More particularly, tip 70 is coupled to distal delivery end 33 of dual barrel cartridge 30 by collar 60 that engages claws 50a–b that extend from dual barrel cartridge 30. Each claw 50a–b has an extension 51a–b and a locking tab 52a–b. Each extension 51a–b extends perpendicularly from a flat engaging surface 54 of dual barrel cartridge 30 at its distal delivery end 33. Note that a portion of flat engaging surface 54 spans between the distal delivery ends 33a–b of barrels 34a–b, this portion is referred to herein as an orientation blocker 56. The optional orientation blocker 56 is opposite from an orientation groove 58 between barrels 34a–b that is used in conjunction with an orientation member 72 of tip 70 as described below.

Collar 60 can be employed to selectively couple tip 70 to dual barrel cartridge 30. In order to couple tip 70 to dual barrel cartridge 30, proximal coupling end 71 of tip 70 can be mounted onto nipple 40 of cartridge 30, after which collar 60 is selectively coupled to claws 50a–b. More particularly, tip 70 is coupled to cartridge 30 upon mounting proximal coupling end 71 of tip 70 onto nipple 40, then placing collar 60 over proximal end 71 of tip 70, then turning collar 60 a quarter turn with respect to claws 50a–b so that collar 60 is twisted under claws 50a–b. Thus, claws 50a–b grasp the collar 60. This configuration enables collar 60 to tightly seal the connection between tip 70 and cartridge 30 such that material does not seep between the connection.

With continued reference to FIGS. 1–6, proximal coupling end 71 of delivery tip 70 selectively seats within collar 60. Collar 60 has a rim 61 that defines an aperture 62 that is centrally located in collar 60. Stop ridges 63a–b extend from rim 61 with a configuration that is generally tangential with respect to rim 61. Rim 61 and stop ridges 63a–b extends perpendicularly upward from wings 64a–b. Wing 64a is opposite from wing 64b.

Each wing 64a–b has a tapered portion 65a–b opposite from the stop ridge on that wing 64a–b. As best seen in FIG. 1, each tapered portion 65a–b increases in thickness until its thickness is the same as that of flat portions 66a–b. This configuration enables opposing wings 64a–b of coupler 60 to be respectively grasped by opposing claws 50a–b of cartridge 30 in the manner of a quarter turn fastener, the tapered portion 65a–b of each wing 64a–b sliding under the respective claw 50a–b first, followed by the flat portion 66a–b. Stop ridges 63a–b are configured to abut claws 50a, 50b of cartridge 30 after the flat portions 66a–b are slid under the claws 50a–b during assembly. More particularly, stop ridges 63a–b extend from respective wings 212a, 212b with a configuration that enables them to stop the movement of the wings as stop ridges 214a–b abut against the respective claws. While a single stop ridge may be employed, two ridges are preferred. Stop ridges 63a–b preferably have curved distal ends such that when the collar is positioned on distal delivery end 33 of dual barrel cartridge 30, collar 60 has a cross-sectional shape that is generally similar to the cross-sectional shape of distal delivery end 33.

Collar 60 also has an annular groove 67 that engages an annular rim 75 of tip 70. More particularly, as shown best in FIGS. 3–6, annular groove 67 is sized to fit around annular rim 73 of tip 70. Collar 60 also has a lip 68 which has a smaller diameter than annular groove so tip 70 cannot be pulled through aperture 62 once lip 68 is engaged against annular rim 73. Note that aperture 62, as defined by rim 61 and lip 68 has a diameter that corresponds with the largest diameter of hub 74 of tip 70. Another feature of collar 60 is a flat engaging surface 69 that engages flat engaging surface 54 of dual barrel cartridge 30.

After the features of tip 70 are fully explained then the flow path of materials A and B are explained. Tip 70 is best understood with reference to FIGS. 1–6 for general orientation and with reference to FIGS. 9-11 B for specific details. The primary components of tip 70 include a hub 74 having a delivery chamber 80, and a mixing element housing 90 containing a mixing element 92. Tip 70 has a mixed material outlet 99 at its distal delivery end 93 opposite from delivery chamber opening 76 at proximal coupling end 71.

As discussed above, proximal coupling end 71 of tip 70 selectively mounts on nipple 40 of cartridge 30. As also indicated above, the coupling is preferably achieved through the use of an optional orientation member 72. Note that in the absence of orientation blocker 56, a tip that has an optional orientation member may be coupled in one of two possible positions on nipple 40. Of course, the configuration can also be reversed such that there is an orientation member extending from cartridge 30 that is received into a corresponding orientation receptacle in the tip.

Annular rim 73 extends perpendicularly from the sidewalls 75 of hub 74. As indicated above, annular rim 73 engages lip 68 and annular groove 67 of collar so that collar 60 can hold tip 70 on dual barrel cartridge 30. Delivery chamber opening 76 of hub 74 is defined by sidewalls 75 of hub 74.

Hub 74 has a hub shoulder 77 from which mixing element housing 90 integrally extends. Mixing element housing 90 defines a mixing chamber inlet 78 that is the opening into mixing chamber 91. Hub shoulder 77 extends radially inward from sidewalls 75 to mixing chamber inlet 78. This configuration permits the use of a mixing chamber 91 with a smaller diameter than the diameter of receiving chamber 80, thereby minimizing the amount of materials introduced into mixing chamber 91. By minimizing the amount of materials introduced into mixing chamber 91, there is less waste of the materials when tip 70 is discarded after completion of the dental procedure or other procedure utilizing a two-component mixture. However, it is also possible to have a hub that gradually tapers toward the mixing element housing 90 or to have the elements sized such that there is no need for a shoulder between the hub and the mixing element housing.

Figure 9:
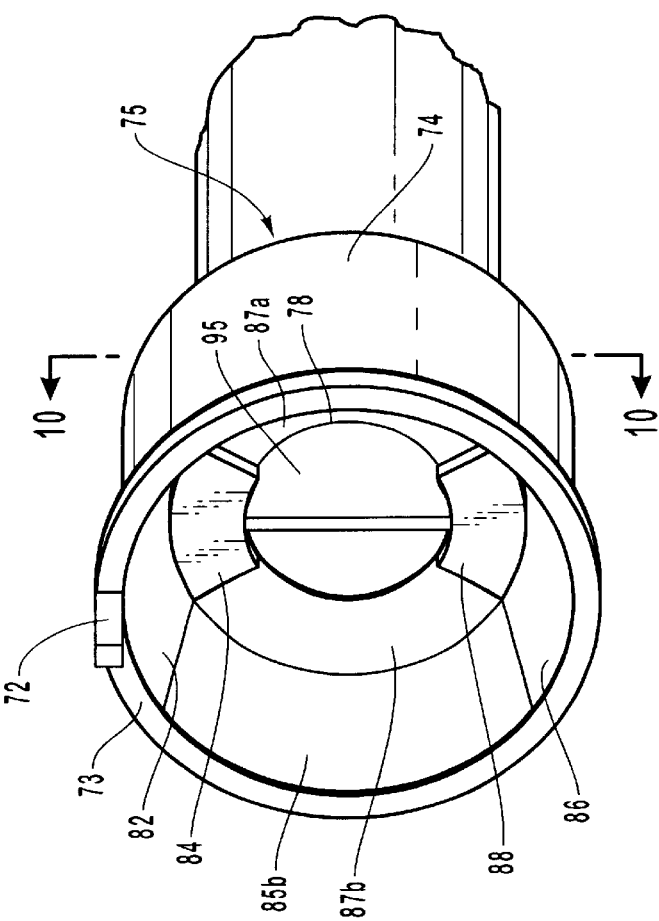
FIG. 9 demonstrates a rear view of the hub of the delivery tip shown in FIG. 1. demonstrates a side view of the delivery tip of FIG. 1 featuring a lumen of the tip in phantom lines.
Figure 11A:
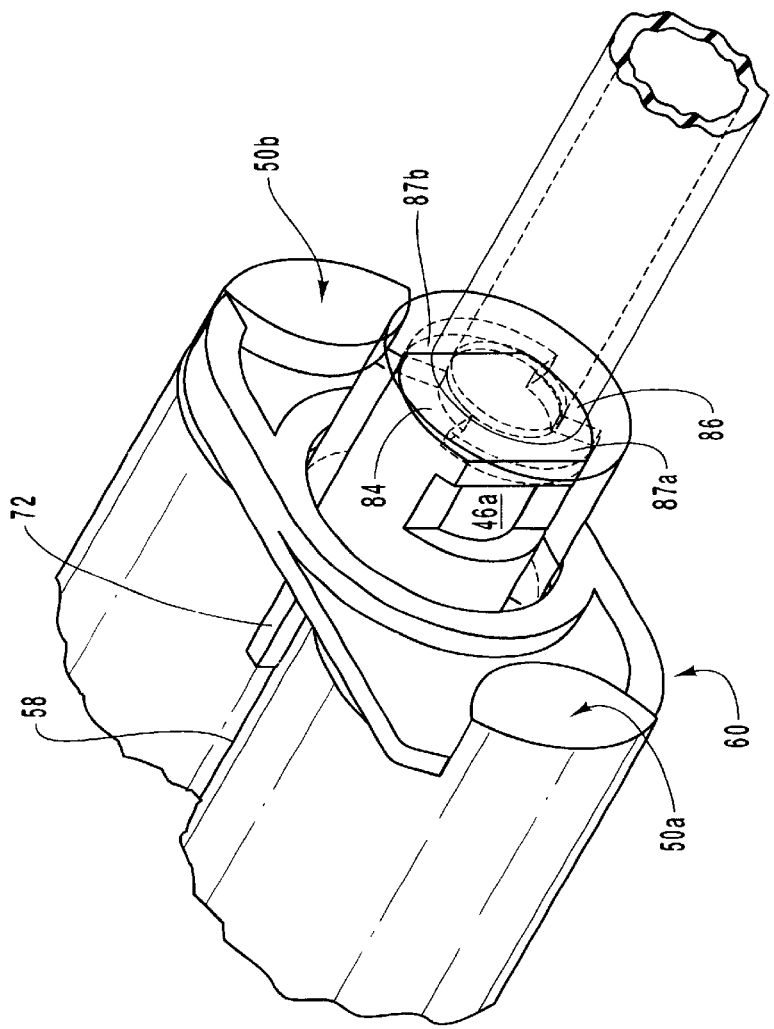
FIG. 11A is a perspective view of nipple with the delivery chamber of the tip drawn with phantom lines to depict the flow paths out of the side portals, along the side channels and then through the shoulder funnels to the delivery chamber opening.

Delivery chamber 80 is the space within hub 74 that is defined by sidewalls 75 and hub shoulder 77 of hub 74. The interior surfaces of sidewalls 75 and shoulder 77 are uniquely configured to provide a tight seal with nipple 40 and to provide two distinct flow paths in delivery chamber 80 of hub 74. As best seen in FIG. 9, these interior surfaces include opposing recessed portions of the interior surfaces of sidewalls 75 and hub shoulder 77 between opposing raised portions of the interior surfaces of the sidewalls 75 and hub shoulder 77. More particularly, the opposing recessed portions of the interior surfaces of sidewalls 75 are referred to as sidewall channels and are identified as 85a–b and the opposing recessed portions of the interior surfaces of hub shoulder 77 are referred to as shoulder funnels and are identified as 87a–b. The opposing raised portions of the interior surfaces of sidewalls 75 are identified as 82 and 86 and the opposing raised portions of the interior surfaces of hub shoulder 77 are identified as 84 and 88.

As shown in FIGS. 3–6 and FIGS. 11A–B, when nipple 40 is inserted into delivery chamber 80 of tip 70 with orientation member 72 inserted into orientation groove 58, side portals 46a–b are respectively positioned opposite from opposing sidewall channels 85a–b. As shown in FIG. 9, the opposing sidewall channels 85a–b are aligned with the opposing shoulder funnels 87a–b such that there is a separate pathway for each material from each side portal 46a–b to mixing chamber inlet 78. After materials A and B pass out of side portals 46a–b and against sidewall channels 85a–b then the materials pass around truncated flanges 42a–b, against shoulder funnels 87a–b and through mixing chamber inlet 78. Note that the opposing raised sidewall portions 82 and 86 are aligned with the opposing raised shoulder portions 84 and 88 in order to form a seal with sidewalls 45 and flat sealing head 42 of nipple 40 once nipple 40 is inserted into delivery chamber 80.

The separate flow paths of materials A and B are preferably maintained until after the materials are in mixing element 92. Any known mixing element may be utilized that has an appropriate configuration for enabling static mixing of materials A and B within mixing element housing 90. As best seen in FIGS. 3–4, mixing element 92 preferably has a plurality of stationary mixing vanes with alternating right-hand and left-hand twists that are fixed in position. Mixing element 94 is preferably integrally formed.

Figure 10:
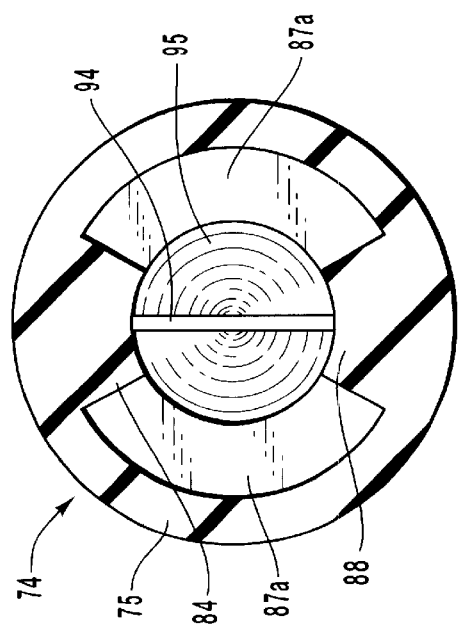
FIG. 10 is a transverse cross-sectional view of the shoulder of the tip shown in FIG. taken along cutting lines 10—10 in FIG. 9 to depict the configuration of the shoulder funnels and the opposing raised shoulder portions.
Figure 11B:
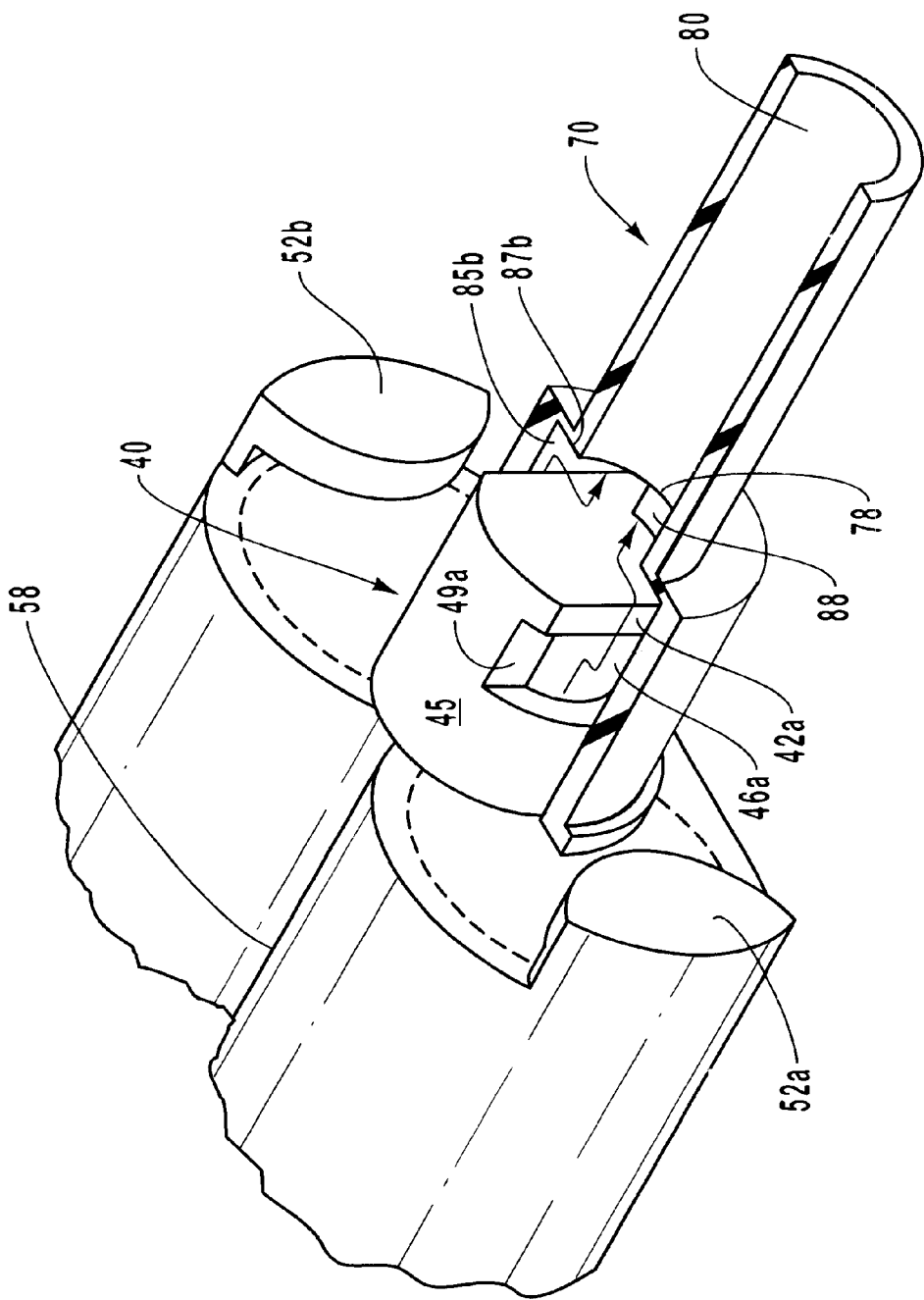
FIG. 11B is a perspective view with a partial cut-away to depict the flow paths out of the side portals, along the side channels and then through the shoulder funnels to the delivery chamber opening.

As shown in FIGS. 5–6, mixing element 92 is preferably positioned such that its proximal end is positioned in mixing chamber inlet 78. Additionally, as best seen in FIG. 5 and FIGS. 9–10, mixing element 92 is preferably configured such that the first vane is a septum vane 95 that maintains separate flow paths for materials A and B until the materials is reach the second vane 96. More particularly, vane 95 has a leading edge 94 that is positioned such that it extends between the opposing raised shoulder portions 84 and 88 and is centered on the opposing raised shoulder portions 84 and 88. Note that leading edge 94 is flush with the opposing raised shoulder portions 84 and 88 and extends slightly beyond shoulder funnels 87a–b. This configuration enables leading edge 94 and the opposing raised shoulder portions 84 and 88 to seal against flat sealing head 42 of nipple 40.

Opposing raised sidewall portions 82 and 86 also form a seal with the sidewalls 45 of nipple 40 from its receiving end 41 to its terminal end 43 as shown in FIG. 6. The width of opposing raised sidewall portions 82 and 86 corresponds with the width between the sides of side portals 46a–b so that opposing raised sidewall portions 82 and 86 form a seal with the portions of sidewalls 45 between side portals 46a–b. As discussed above, these portions of side walls 45 include seal extensions 49a–b and the portions of sidewalls 45 from which septum 47 extends. Of course, in the event that side portals 46a–b are so wide that there are no seal extensions 49a–b then opposing raised sidewall portions 82 and 86 are narrower and correspond only with the thickness of septum 47.

The potential for cross-contamination that may ruin materials A and B that are still in dual barrel cartridge 30, particularly in nipple 40, is minimized by mixing far away from side portals 46a–b. The seal formed between opposing raised sidewall portions 82 and 86 with the sidewalls 45 of nipple 40 ensures that materials A and B advance in sidewall channels 85a–b and around truncated flanges 42a–b. The seal prevents either material from going around sidewalls 45 and into the side portal of the other material. The advantages of this seal are enhanced by the seal between leading edge 94 and the opposing raised shoulder portions 84 and 88 with flat sealing head 42 of nipple 40. The seal at flat sealing head 42 prevents either material from contacting each other by passing over flat sealing head 42. The combination of these seals with the position of leading edge 94 of first vane 95 enables the mixing to occur downstream after passing beyond first vane 95 while minimizing or eliminating premature intermingling of one material with the other.

Of course, other embodiments are possible that do not include all of the features that maximize the distance between side portals 46a–b and the downstream point at which the materials contact each other. For example, mixing element 92 may be recessed such that leading edge 94 is not flush with opposed raised shoulder portions 84 and 88 such that materials A and B contact each other as they enter first vane 95. While mixing element 92 may be recessed any distance in such a configuration, it is preferable to minimize this distance as it results in some wasted materials. It is also possible to have a first vane with a leading edge that is not in alignment to maintain the separate flow paths. Such a misaligned leading edge is not coplanar with septum 47 and is not positioned such that mixing chamber inlet 78 is divided with one half facing shoulder funnel 87a and the other half facing shoulder funnel 87b. Additionally, it is possible to have a hub with a delivery chamber 80 that is longer than nipple 40 such the materials contact each other after passing around truncated flanges 42a–b or around septum 47.

Mixing element housing 90 has a generally tapered exterior. However, the mixing element 92 has generally the same diameter along its length so the thickness of the sidewalls of mixing element housing 90 taper in thickness from hub 74 to distal delivery end 93. Distal delivery end 93 may have any suitable configuration. However, mixing element housing 90 preferably tapers abruptly, as shown, at a distal shoulder 97 to a delivery neck extension 98. Distal shoulder assists in holding mixing element 92 in place within mixing chamber 91. Delivery neck extension 98 is tubular and terminates at a mixed material outlet 99 from which the mixed material is delivered.

Cap 170 will now be discussed in additional detail with reference to FIGS. 12–15. Cap 170 has a proximal coupling end 171 opposite from a distal grasping end 174. Like tip 70, cap 170 has an optional orientation member 172 extending from annular rim 173. Annular rim 173 extends perpendicularly and integrally from the sidewalls 175 of cap 170. Like annular rim 73 of tip 70, annular rim 173 engages lip 68 and annular groove 67 of collar so that collar 60 can hold cap 170 on dual barrel cartridge 30.

Cap 170 has a nipple chamber opening 176 at its proximal coupling end 171 that is defined by sidewalls 175. Nipple chamber opening 176 provides access into nipple chamber 180 which is sized to receive nipple 40. Nipple chamber 180 is defined by the interior surfaces of sidewalls 175 and by stop 178. Stop 178 divides cap 170 such that there is a nipple chamber 180 and an extension chamber 182. Stop 178 is flat for engagement against flat sealing head 42 of nipple 40. The portion of cap 170 beyond stop 178 is essentially an extension portion 179 that enables the cap to be easily grasped. Since the primary purpose of the extension portion 179 is for easy grasping, it is hollow to minimize the amount of material that is utilized.

Figure 15:
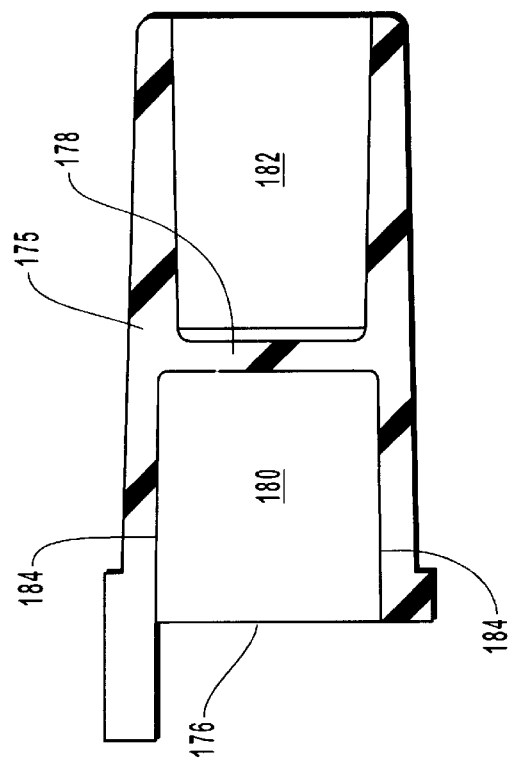
FIG. 15 is an enlarged, cross-sectional view of the cap shown in FIGS. 13–14 taken along cutting lines 15—15 in FIG. 13 to depict the same elements shown in FIG. 14 from a different plane.
Figure 14:
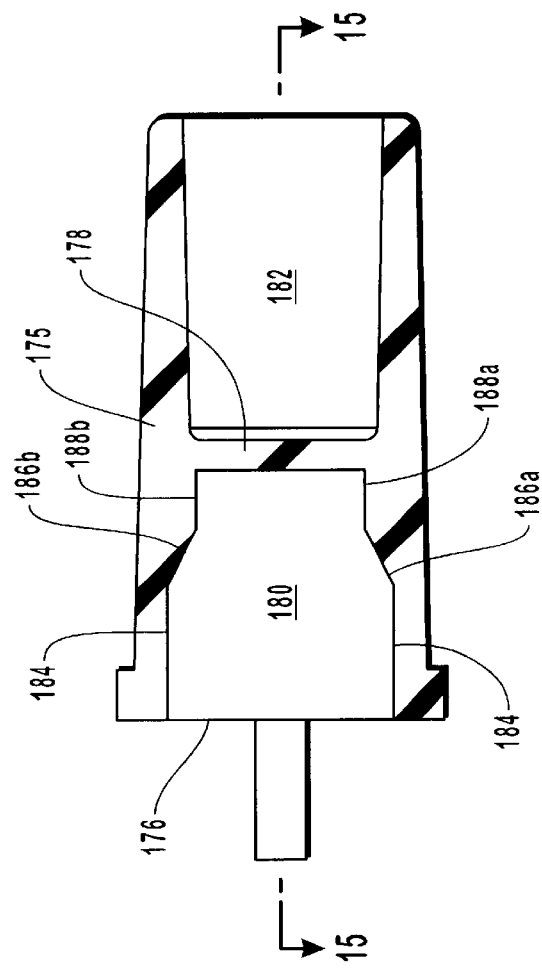
FIG. 14 is an enlarged, cross-sectional view of the cap shown in FIGS. 13–14 taken along cutting lines 14—14 in FIG. 13.

Nipple chamber 180 is shaped in a complimentary shape to that of nipple 40 as shown in FIGS. 14–15. FIG. 14 provides a longitudinal view of cap 170 that shows the configuration of the portions of nipple chamber 180 that engage side portals 46a–b. Note that the cross-sectional shape of nipple chamber 180 when cap 170 is cut longitudinally through orientation member 172 as shown in FIG. 15, corresponds with the tapered cylindrical shape of nipple 40 in between side portals 46a–b. The interior surfaces of sidewalls 175 that define the shape of nipple chamber 180 include nipple sidewall engagement surface 184 that has a slight taper corresponding with the tapered sidewalls 45 of nipple 40. The diameter of nipple chamber 180 decreases at opposing shoulder surfaces 186a–b which are transitions to opposing neck surfaces 188a–b. In between shoulder surfaces 186a–b and neck surfaces 188a–b, nipple sidewall engagement surface continues from nipple chamber opening 176 to stop 178. The shoulder surface 186a and neck surface 188a engage side portal 46a while shoulder surface 186b and neck surface 188b engage side portal 46b.

Cap 170 provides tight seals that prevent one of the materials from passing over flat sealing head 42 or around sidewalls 175 and contacting the other material. As indicated above, stop 178 is flat for engagement against flat sealing head 42 of nipple 40. These flat surfaces form a seal that prevents one of the materials from passing over or around flat sealing head 42 and cross-contaminating the other material. Of course, stop 178 may have any shape that is complimentary with the shape of sealing head 42. The nipple sidewall engagement surface 184 tightly engages the tapered sidewalls 45 of nipple 40 at their respective lower halves and also in between side portals 46a–b to form a seal. This seal prevents a material from escaping out of a nipple side portal and passing around nipple 40 into contact with the other material. Note that side portals 46a–b may be more closely engaged by designing the opposing shoulder surfaces of nipple chamber 180 to extend perpendicularly inward instead of tapering toward opposing necks 188a–b such that the perpendicular shoulder surfaces abut the bottoms of the respective side portals 46a–b. Additionally, elimination of flanges 42a–b enable side portals 46a–b to be essentially plugged. Although, side portals 46a–b are not plugged by the embodiment shown in the drawings, the seals described above prevent cross-contamination.

Since cap 170 is configured to be selectively, removably mounted onto nipple 40, syringe system 10 can be utilized to deliver two mixed materials and then be resealed on a repeated basis until all of the two materials have been fully used. Cap 170 may alternatively be tethered to collar 60. By tethering collar 60 to cap 190, cap 190 is less likely to become lost or misplaced.

Plunger unit 20 is an example of plunger means for applying pressure to the first and second materials held in the barrels of the dual barrel cartridge. Dual barrel cartridge 30 is an example of barrel means for holding the first and second materials in separate barrels until pressure is applied with sufficient force to direct the first and second materials out of barrel outlets. Dual lumen nipple 40 is an example of dual lumen nipple means for receiving the first and second materials into separate lumens from the barrel means and delivering the first and second materials out of side portals in the lumens, wherein the dual lumen nipple means extends integrally from the barrel means. Collar 60 and claws 50 are together an example of means for selectively coupling the delivery tip means to a barrel means. Delivery tip 70 is an example of a static mixer delivery tip means for mixing the first and second materials together after separately receiving the first and second materials from the dual lumen nipple means. Cap 170 is an example of a cap means for sealing the dual lumen nipple after the delivery tip has been removed from the dual lumen nipple.

The materials utilized to form the elements described herein may be comprised of a variety of different suitable materials. Examples of suitable materials include polypropylene, polycarbonate, or polyethylene, thermosetting materials, thermoplastic elastomers, and neoprene.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by united states Letters Patent is:

1. A syringe system for mixing first and second materials together and delivering the mixed materials, comprising:
    barrel means for holding the first and second materials in separate barrels until pressure is applied with sufficient force to direct the first and second materials out of barrel outlets;
    dual lumen nipple means for receiving the first and second materials into separate lumens from the barrel means and delivering the first and second materials out of side portals in the lumens, wherein the dual lumen nipple means extends integrally from the barrel means;
    static mixer delivery tip means for mixing the first and second materials together after separately receiving the first and second materials from the dual lumen nipple means; wherein the delivery tip means has a hub with sidewalls that define a delivery chamber and a delivery chamber opening; wherein a mixing element housing extends from the hub, houses a mixing element, defines a mixing chamber, a mixing chamber inlet that is opposite from the delivery chamber opening and a mixed material outlet opposite from the mixing chamber inlet; wherein the delivery chamber is in fluid communication with the mixing chamber via the mixing chamber inlet, wherein the delivery chamber is sized to releasably receive the nipple means, the sidewalls of the hub having interior surfaces that include opposing raised sidewall portions between opposing sidewall channels, each opposing raised sidewall portions having sufficient width to form a seal with the sidewalls of the nipple once the nipple is inserted into the delivery chamber, each opposing sidewall channel being adapted such that when the nipple is inserted into the delivery chamber with each side portal opposite from each recessed sidewall portion the material delivered out of each side portal is channeled to the mixing chamber inlet, and
    means for selectively coupling the delivery tip means to the barrel means.

2. A syringe system as recited in claim 1, further comprising plunger means for applying pressure to the first and second materials held in the separate barrels of the barrel means.

3. A syringe system as recited in claim 1, further comprising a cap means for sealing the dual lumen nipple means after the delivery tip means has been removed from the dual lumen nipple means.

4. A syringe system as recited in claim 1, wherein the dual lumen nipple means has a sealing head at its terminal end extending from a septum and a portion of the sidewalls.

5. A syringe system as recited in claim 1, wherein the dual lumen nipple means has a flat sealing head at its terminal end extending from a septum and a portion of the sidewalls, wherein the flat sealing head has truncated flanges that extend-perpendicularly relative to the septum, wherein each truncated flange has a length that permits the material delivered out of each side portal to pass around the truncated flange when the dual lumen nipple means is inserted into the delivery chamber of the delivery tip means.

6. A syringe system as recited in claim 1, wherein the hub of the delivery tip means has a hub shoulder extending inward from the sidewalls of the hub to the mixing element housing.

7. A syringe system as recited in claim 6, wherein the hub shoulder has interior surfaces that include opposing raised shoulder portions between opposing shoulder funnels, wherein each opposing raised shoulder portion is aligned with one of the opposing raised sidewall portions and each opposing shoulder funnel is aligned with one of the opposing sidewall channels.

8. A syringe system as recited in claim 1, wherein the mixing element has a first vane with a leading edge positioned in the mixing chamber inlet.

9. A syringe system as recited in claim 7, wherein the mixing element has a first vane with a leading edge that is positioned such that the leading edge extends between the opposing raised shoulder portions, is centered on the opposing raised shoulder portions and is flush with the opposing raised shoulder portions while extending slightly beyond the opposing shoulder funnels.

10. A syringe system for mixing first and second materials together and delivering the mixed materials, comprising:
    a dual barrel cartridge having a proximal grasping end opposite from a distal delivery end, the dual barrel cartridge including first and second barrels; each barrel having an opening at the proximal grasping end of the dual barrel cartridge and a barrel outlet at the distal delivery end of the dual barrel cartridge; the dual barrel cartridge having opposing claws at its distal delivery end;
    a dual lumen nipple having a receiving end opposite from a terminal end, the dual lumen nipple having cylindrical sidewalls extending integrally from the distal delivery end of the dual barrel cartridge; the dual lumen nipple having a first and a second lumen that are separate from each other and are respectively in fluid communication with the first and second barrels through the respective barrel outlets; the sidewalls being partially terminated such that each lumen has a side portal; each side portal having a bottom and sides that are defined by the sidewalls;

a delivery tip having a proximal coupling end opposite from a distal delivery end; the delivery tip having a hub at its proximal coupling end that is integrally connected to a mixing element housing that houses a mixing element; the hub having sidewalls that define a delivery chamber and a delivery chamber opening; the mixing element housing defining a mixing chamber, a mixing chamber inlet that is opposite from the delivery chamber opening and a mixed material outlet opposite from the mixing chamber inlet; the delivery chamber being in fluid communication with the mixing chamber via the mixing chamber inlet; the delivery chamber being sized to releasably receive the nipple; the sidewalls of the hub having interior surfaces that include opposing raised sidewall portions between opposing sidewall channels; each opposing raised sidewall portions having sufficient width to form a seal with the sidewalls of the nipple once the nipple is inserted into the delivery chamber; each opposing sidewall channel being adapted such that when the nipple is inserted into the delivery chamber with each side portal opposite from each sidewall channel the material delivered out of each side portal is channeled to the mixing chamber inlet; and a removable collar adapted to hold the nipple in the receiving chamber once the tip has been inserted though an aperture of the removable collar and the collar locked under the claws of the dual barrel cartridge.

11. A syringe system as recited in claim 10, further comprising a plunger unit having two plungers adapted for insertion into the first and second barrels of the dual barrel cartridge.

12. A syringe system as recited in claim 10, further comprising a cap for insertion over the nipple after the delivery tip has been removed.

13. A syringe system as recited in claim 10, wherein the first and second lumens are separated by a septum extending integrally from the distal delivery end of the dual barrel cartridge and across the sidewalls such that the first and second lumens are defined by the sidewalls and the septum.

14. A syringe system as recited in claim 13, wherein the dual lumen nipple has a sealing head at its terminal end extending from the septum and a portion of the sidewalls.

15. A syringe system as recited in claim 13, wherein the dual lumen nipple has a flat sealing head at its terminal end extending from the septum and a portion of the sidewalls, wherein the flat sealing head has truncated flanges that extend perpendicularly relative to the septum, wherein each truncated flange has a length that permits the material delivered out of each side portal to pass around the truncated flange when the nipple is inserted into the delivery chamber of the tip.

16. A syringe system as recited in claim 10, wherein the hub of the delivery tip has a hub shoulder extending inward from the sidewalls of the hub to the mixing element housing.

17. A syringe system as recited in claim 16, wherein the hub shoulder has interior surfaces that include opposing raised shoulder portions between opposing shoulder funnels, wherein each opposing raised shoulder portion is aligned with one of the opposing raised sidewall portions and each opposing shoulder funnel is aligned with one of the opposing sidewall channels.

18. A syringe system as recited in claim 10, wherein the mixing element has a first vane with a leading edge positioned in the mixing chamber inlet.

19. A syringe system as recited in claim 17, wherein the mixing element has a first vane with a leading edge that is positioned such that the leading edge extends between the opposing raised shoulder portions, is centered on the opposing raised shoulder portions and is flush with the opposing raised shoulder portions while extends slightly beyond the opposing shoulder funnels.

20. A syringe system for mixing first and second materials together and delivering the mixed materials, comprising:

a dual barrel cartridge having a proximal grasping end opposite from a distal delivery end, the dual barrel cartridge including first and second barrels; each barrel having an opening at the proximal grasping end of the dual barrel cartridge and a barrel outlet at the distal delivery end of the dual barrel cartridge, the dual barrel cartridge having opposing claws at its distal delivery end;

a dual lumen nipple having a receiving end opposite from a terminal end; the dual lumen nipple having cylindrical sidewalls extending integrally from the distal delivery end of the dual barrel cartridge; the dual lumen nipple having a septum extending integrally from the distal delivery end of the dual barrel cartridge and across the sidewalls such that the dual lumen nipple has first and second lumens defined by the sidewalls and the septum; the first and second lumens are respectively in fluid communication with the first and second barrels through the respective barrel outlets; the sidewalls being partially terminated such that each lumen has a side portal; each side portal having a bottom and sides that are defined by the sidewalls; each side portal having a top defined by a flat sealing head that extends at the terminal end of the dual lumen nipple from the septum and a portion of the sidewalls; the flat sealing head having truncated flanges that extend perpendicularly relative to the septum; each truncated flange having a length that permits the material delivered out of each side portal to pass around the truncated flange when the nipple is inserted into the delivery chamber of the tip;

a delivery tip having a proximal coupling end opposite from a distal delivery end; the delivery tip having a hub at its proximal coupling end that is integrally connected to a mixing element housing that houses a mixing element; the hub having hub sidewalls and a hub shoulder extending inward from the hub sidewalls to the mixing element housing, the hub having a delivery chamber defined by the hub sidewalls and the hub shoulder and having a delivery chamber opening defined by the hub sidewalls; the mixing element housing defining a mixing chamber, a mixing chamber inlet that is opposite from the delivery chamber opening and a mixed material outlet opposite from the mixing chamber inlet; the delivery chamber being in fluid communication with the mixing chamber via the mixing chamber inlet, the delivery chamber being sized to releasably receive the nipple; the hub sidewalls having interior surfaces that include opposing raised sidewall portions between opposing sidewall channels, the hub shoulder having interior surfaces that include opposing raised shoulder portions between opposing shoulder funnels; the opposing raised sidewall portions and the opposing raised shoulder portions being aligned and adapted to form a seal with the sidewalls and the flat sealing head of the nipple once the nipple is inserted into the delivery chamber, the opposing sidewall channels being aligned with the opposing shoulder funnels such that there is a separate pathway for each material from each side portal to the mixing chamber inlet; and a removable collar adapted to hold the nipple in the receiving chamber once the tip has been inserted though an aperture of the removable collar and the collar locked under the claws of the dual barrel cartridge.

21. A syringe system as recited in claim 19, further comprising a plunger unit having two plungers adapted for insertion into the first and second barrels of the dual barrel cartridge.

22. A syringe system as recited in claim 19, further comprising a cap for insertion over the nipple after the delivery tip has been removed.

23. A syringe system as recited in claim 9, wherein the mixing element has a first vane with a leading edge that is positioned such that the leading edge extends between the opposing raised shoulder portions, is centered on the opposing raised shoulder portions and is flush with the opposing raised shoulder portions while extends slightly beyond the opposing shoulder funnels.

* * * * *

UNITED STATES PATENT AND TRADEMARK OFFICE
CERTIFICATE OF CORRECTION

PATENT NO. : 6,398,761 B1
DATED : June 4, 2002
INVENTOR(S) : Dan J. Bills, Dan E. Fischer and Bruce S. McLean It is certified that error appears in the above-identified patent and that said Letters Patent is hereby corrected as shown below:

Column 1,
Line 30, after "material therefrom" please insert -- . --

Column 3,
Line 21, after "to the septum" please insert -- . --
Line 66, after "first vane without" replace "contact" with -- contacting --

Column 4,
Line 63, after "tip shown in FIG. 1" delete "."
Line 66, after "tip shown in FIG." please insert -- 9 --

Column 5,
Line 44, before "in cross sectional" replace "FIG. 34" with -- FIGS. 3-4 --

Column 6,
Line 6, after "the use or" delete "a"
Line 24, before "Dual barrel cartridge" delete "is"
Line 30, after "a common septum" insert -- . --
Line 44, before "all the way" replace "extends" with -- extend --

Column 7,
Line 39, after "the slight taper is" delete "."

Column 10,
Line 64, before "reach the second vane" delete "is"

Signed and Sealed this

Twenty-eighth Day of January, 2003

JAMES E. ROGAN
*Director of the United States Patent and Trademark Office*